(12) United States Patent
Tseng

(10) Patent No.: US 6,847,720 B2
(45) Date of Patent: Jan. 25, 2005

(54) QUICK-UPDATING STETHOSCOPE RECEIVER

(76) Inventor: Teng Ko Tseng, 235 Chung-Ho Box 8-24, Taipei (TW)

(*) Notice: Subject to any disclaimer, the term of this patent is extended or adjusted under 35 U.S.C. 154(b) by 0 days.

(21) Appl. No.: 10/316,220

(22) Filed: Dec. 12, 2002

(65) Prior Publication Data

US 2004/0114767 A1 Jun. 17, 2004

(51) Int. Cl.⁷ .............................. A61B 7/04; A61B 7/02
(52) U.S. Cl. .......................... 381/67; 181/131; 181/132
(58) Field of Search ............................ 381/67; 181/131, 181/132; 128/864; 600/528; D24/134

(56) References Cited

U.S. PATENT DOCUMENTS 5,920,038 A * 7/1999 Foster ........................ 181/131
5,945,640 A * 8/1999 Rossini et al. ............... 181/131

* cited by examiner

Primary Examiner—Xu Mei
Assistant Examiner—Laura A. Grier

(57) ABSTRACT

A quick-updating stethoscope receiver comprises a receiver, a listening disk at a lower end of the receiver, the listening disk can be embedded into a lower end of the receiver; an upper cover at a top end of the receiver; and a transducer combining at a lateral wall of the receiver and a connector at a rear end of the transducer. A lower end of the receiver has an axial extended shaft. The shaft is formed with an annular trench. An elastic tightening ring is embedded into the trench. A diameter of a cross section of the tightening ring is larger than a depth of the trench so that part of the tightening ring protrudes out of the trench. A center of the round disk has an opening. By the elastic expanding force of the tightening ring, the round disk is tightly engaged to the shaft so that the round disk can not drop out.

4 Claims, 6 Drawing Sheets

QUICK-UPDATING STETHOSCOPE RECEIVER

FIELD OF THE INVENTION

The present invention relates to stethoscope receivers; and particularly to a quick-updating stethoscope receiver which can be updated rapidly so that the medical members can operate effectively.

BACKGROUND OF THE INVENTION

A prior art stethoscope receiver is illustrated in FIG. 1 and an exploded perspective view of the prior art stethoscope receiver is shown in FIG. 2. In this prior art, the receiver 1 has threaded tubes at an upper and a lower ends 11 and 12 which are screwed to an upper cover 2 and a listening disk 3. A lateral wall of the receiver 1 has a connecting hole 13 for being inserted to a transducer. A rear end of the transducer 4 is connected to a connector 5. A rear end of the connector 5 may be a sound receiving device 51 having one tube or two tubes. The medical member holds the upper cover 2 and the listening disk 3 will contact the stomach or breast of the patient. Since the listening disk 3 often contacts patients so that the use of the listening disk 3 must be confined. That is, after a time period, the listening disk 3 must be detached for sterilization, even the listening disk 3 will be deserted and a new one is updated. Thereby, many listening disks 3 are necessary. Moreover, the listening disks for adults and children are different and thus medical members must update the listening disks frequently.

In the prior art, if it is desired to separate the listening disk from the receiver 1. It is necessary to rotate the listening disk 3 clockwise so that the listening disk is separated from the threaded tube. When it is desired to reinstall the listening disk 3, a screw hole 31 at a center of the listening disk 3 must be aligned to the threaded tube 12 so as to rotate counter-clockwise for fixing. However, to align the listening disk 3 with the threaded tube 12 is difficult and it is often that the listening disk 3 can not be screwed into the lowest portion of the threaded tube 12. As a result, it is possible that the threaded tube 12 will be broken if the listening disk 3 is screwed into the threaded tube in force. Thus, the listening disk 3 is difficult to draw out. Thereby, the listening disk 3 must be drawn out to screw into the threaded tube 12 again. Thus, the operation is tedious and inconvenient.

Next, the upper cover 2 and listening disk 3 are screwed. The upper cover dose not contact the patients and thus it can be used many times and no problem of infection occurs. Moreover, the prior art upper cover has no indication so that the medical members often take an unwanted stethoscope receiver by mistake.

SUMMARY OF THE INVENTION

Accordingly, the primary object of the present invention is to provide a quick-updating stethoscope receiver comprises a receiver; a listening disk at a lower end of the receiver; wherein the listening disk can be embedded into a lower end of the receiver; an upper cover at a top end of the receiver; and a transducer combining at a lateral wall of the receiver and a connector at a rear end of the transducer. A lower end of the receiver has an axial extended shaft. The shaft is formed with an annular trench. An elastic tightening ring is embedded into the trench. The tightening ring is made of rubber material and a diameter of a cross section of the tightening ring is larger than a depth of the trench so that part of the tightening ring protrudes out of the trench. The listening disk includes a staged round disk and a plastic film at a bottom of the round disk. A center of the round disk has an opening. When the shaft at a lower end of the receiver inserts into the opening, an axial surface of the shaft is in surface-contact with the inner wall and the elastic tightening ring is compressed by an inner wall of the opening so as to induce a friction resisting force. By the elastic expanding force of the tightening ring, the round disk is tightly engaged to the shaft so that the round disk can not drop out.

Another object of the present invention is to provide a quick-updating stethoscope receiver, wherein the upper cover of the receiver is integrally formed with the receiver. An outer diameter of the upper cover is larger than that of the receiver; and a top of the upper cover has a groove; a bottom of the groove is flatly placed with a name card and a transparent film pressing the name card.

The various objects and advantages of the present invention will be more readily understood from the following detailed description when read in conjunction with the appended drawing.

BRIEF DESCRIPTION OF THE PREFERRED EMBODIMENTS

Figure 1:
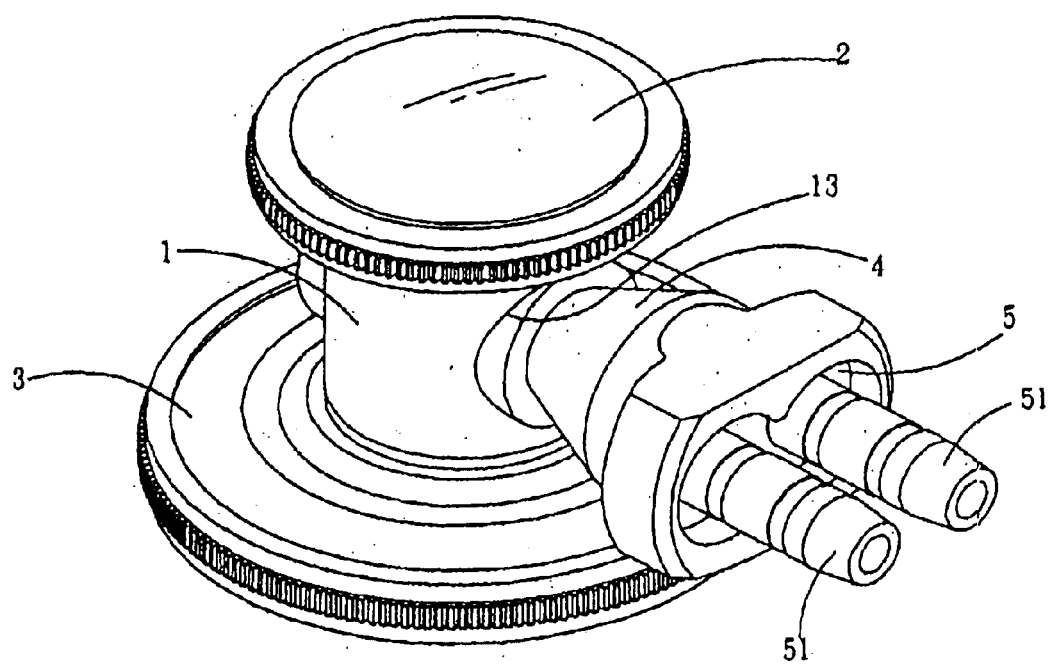
FIG. 1 is an exploded perspective view of a prior art stethoscope receiver.
Figure 2:
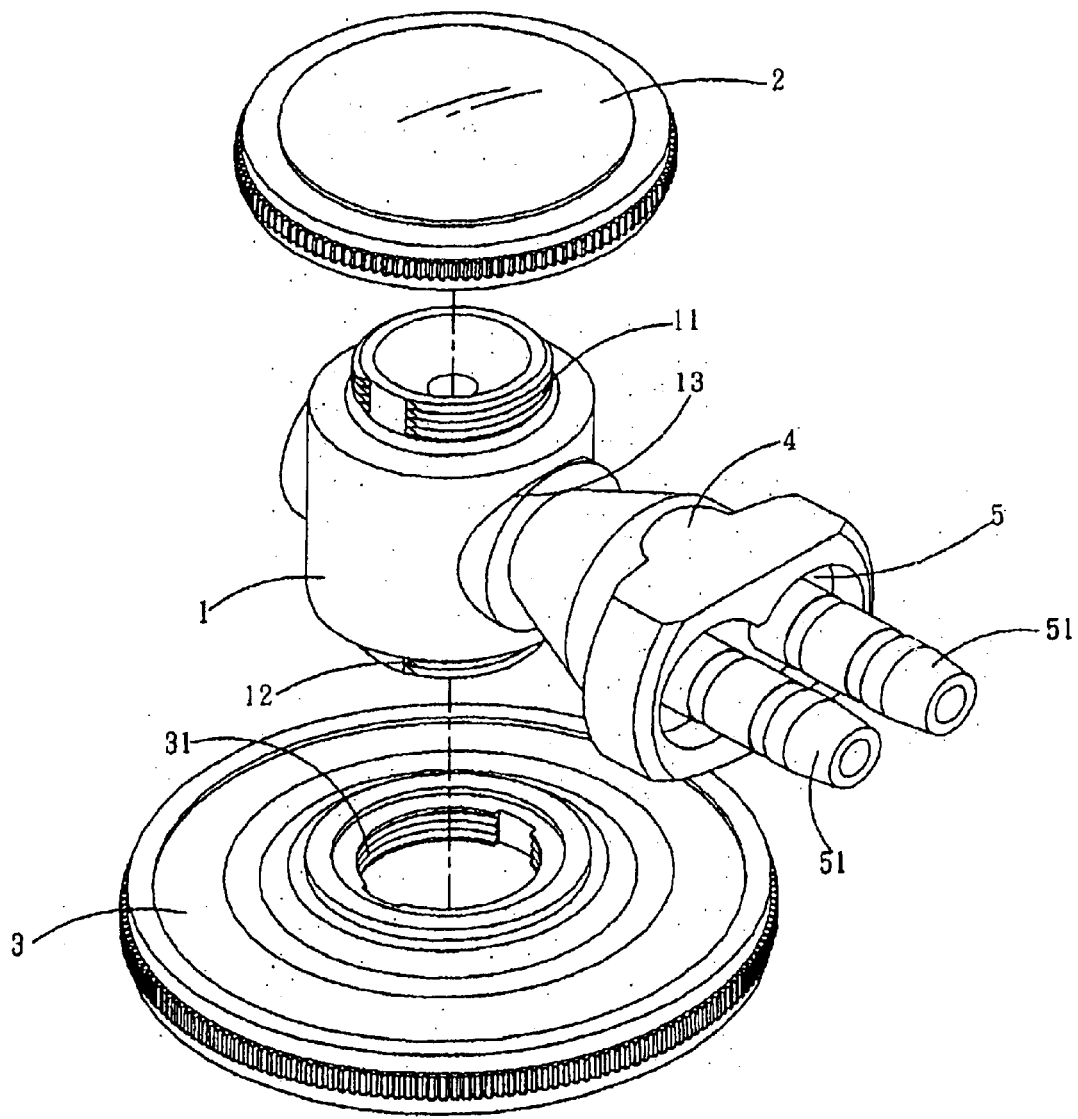
FIG. 2 is an assembled perspective view showing the use of the prior art stethoscope receiver.
Figure 3:
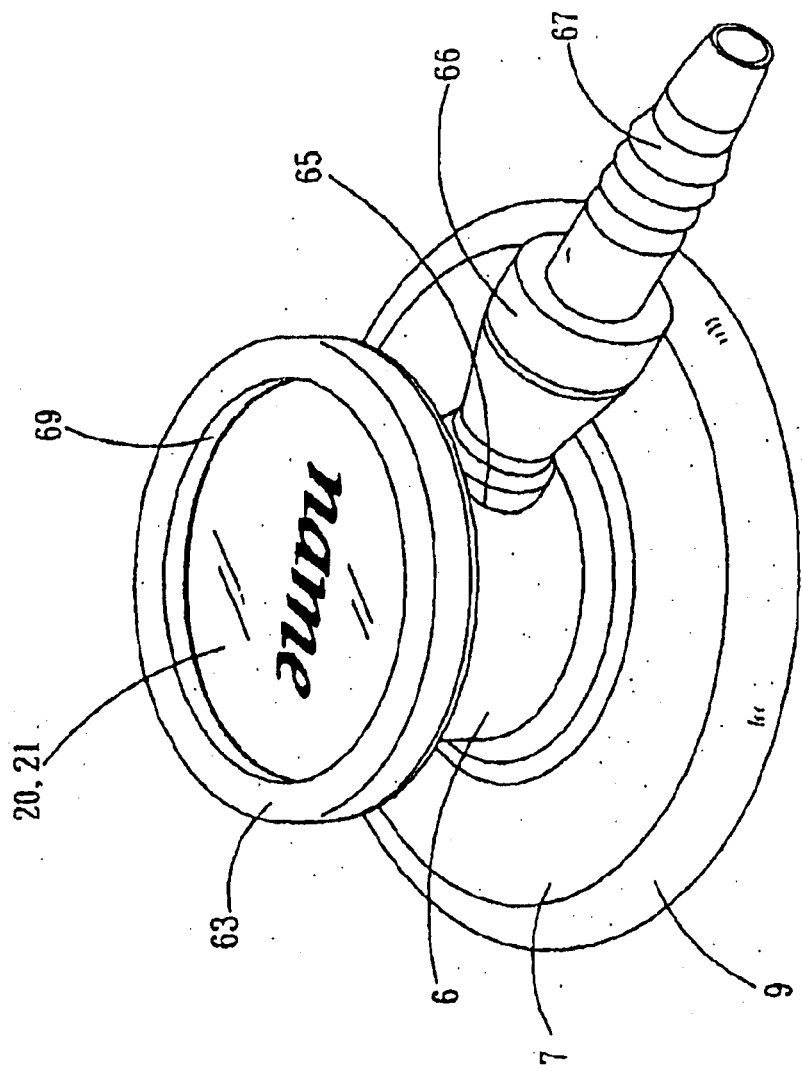
FIG. 3 is an exploded perspective view of the stethoscope receiver of the present invention.
Figure 4:
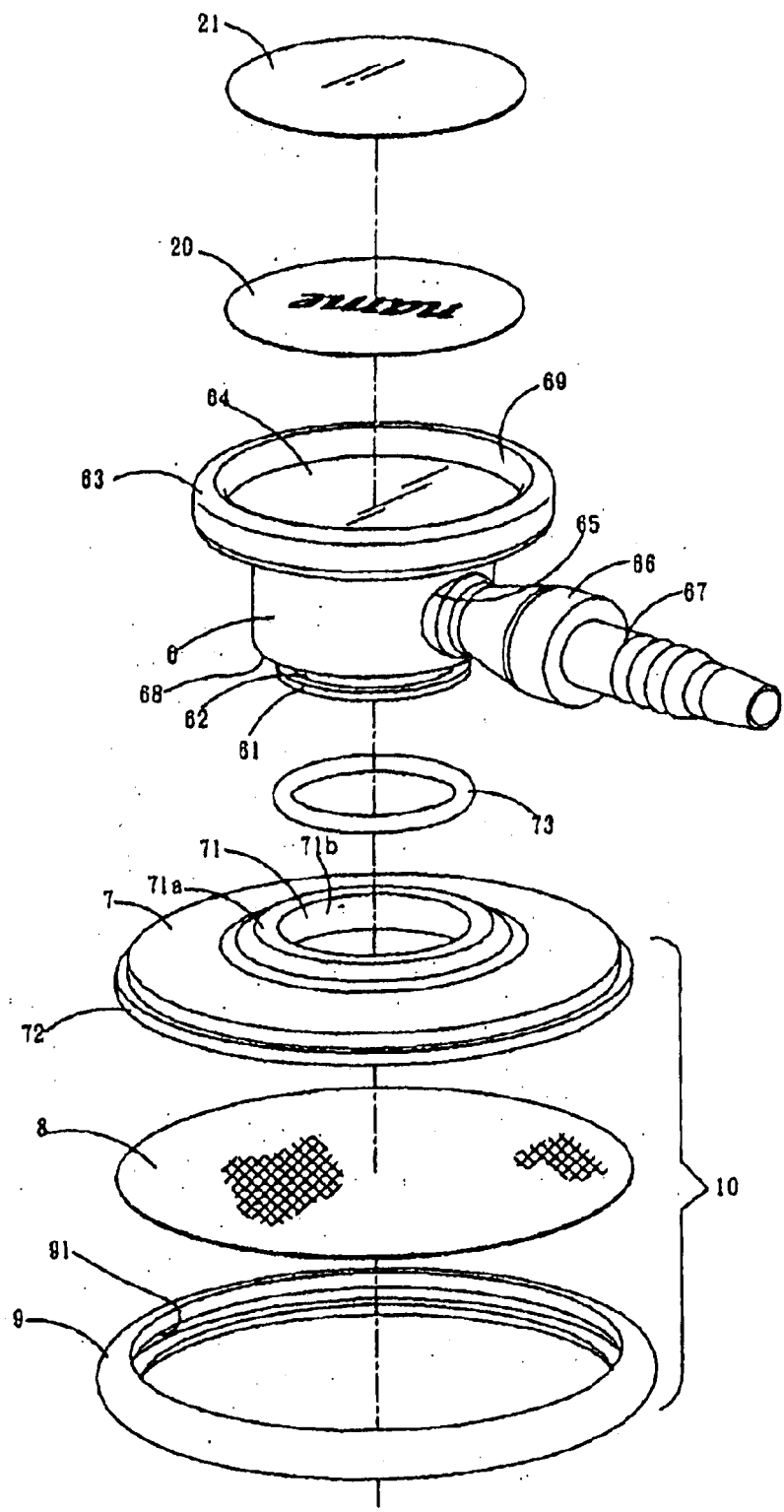
FIG. 4 is an assembled perspective view showing the use of the stethoscope receiver of the present invention.
Figure 5:
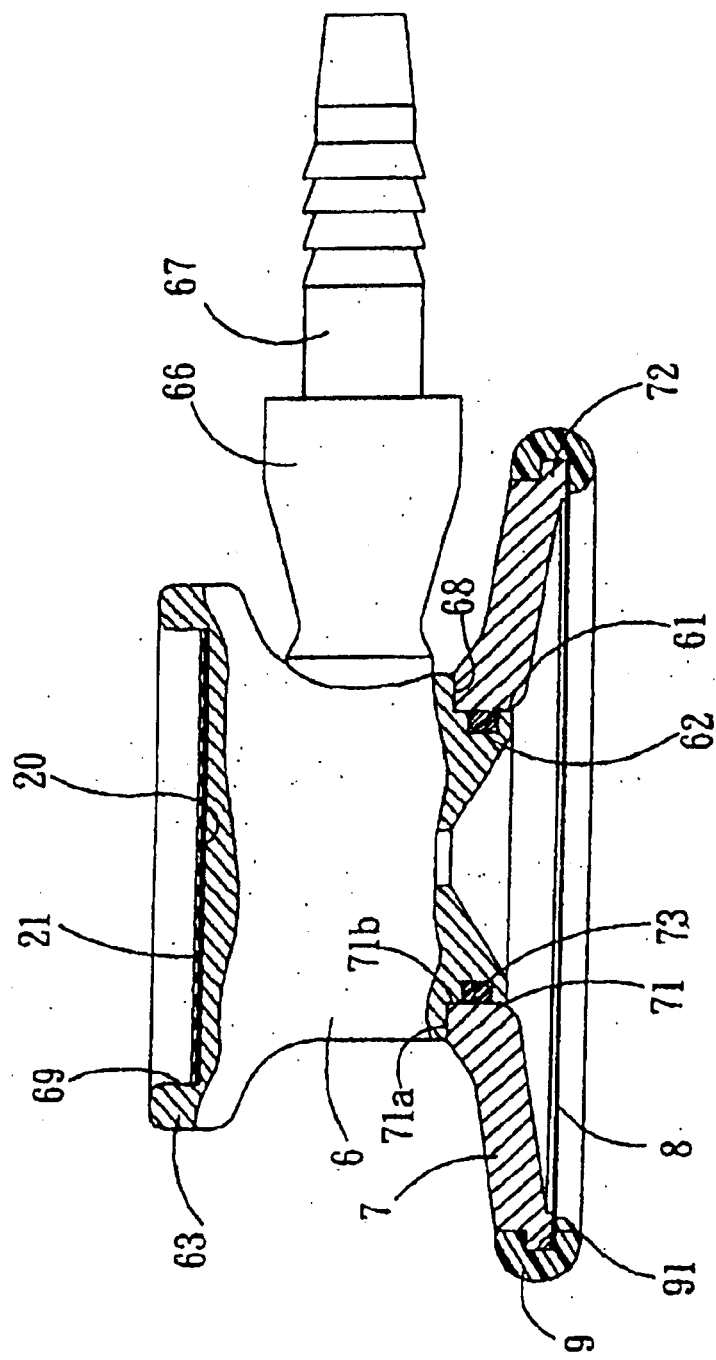
FIG. 5 is a cross sectional view showing the use of the stethoscope receiver of the present invention.

The embodiments of the present invention will be described herein with reference to FIG. 3, in that, a perspective view of the stethoscope receiver of the present invention is illustrated. FIG. 4 shows the exploded perspective view of the stethoscope receiver of the present invention and FIG. 5 shows the cross sectional view of the stethoscope receiver of the present invention.

In the drawings, the structure of the stethoscope receiver includes a receiver 6, a listening disk 10 which can be embedded into a lower end of the receiver 6; an upper cover 63 combining to an upper end of the receiver 6; a transducer 66 combining at a lateral hole 65 of the receiver 6 and a connector 67 at a rear end of the transducer 66. A lower end of the receiver 6 has an axial extended shaft 61. The shaft 61 is formed with an annular trench 62. An elastic tightening ring 73 is embedded into the trench 62. The tightening ring 73 is made of rubber material and the diameter of the cross section of the tightening ring 73 is larger than a depth of the trench 62 so that part of the tightening ring 73 protrudes out of the trench 62. The listening disk 10 includes a staged round disk 7 and a plastic film at a bottom of the round disk 7. There are many ways for fixing the film 8 to the bottom of the round disk 7. For example, an inner edge of the bottom of the round disk 7 is formed with a concave trench (not shown) for embedding the film 8. Or as illustrated in FIG. 5, the film 8 is positioned at a bottom of the round disk 7 and then the elastic rubber ring 9 encloses one periphery of the round disk clamping the film 8. Since the periphery of the round disk 7 is installed with annular flange 72 and an inner edge of the elastic rubber ring 9 is formed with an annular groove 91. The diameter of the film 8 is equal to an outer diameter of the flange 72. Thereby, when the film 8 is at the bottom of the round disk 7, it is flushed with the flange 72. As a result, when the flange 72 of the round disk 7 is embedded into the annular groove 91, the elastic rubber ring 9 will reduce by the elastic force thereof and thus the periphery of the round disk is tightened. This way provides an easy assembled method within a short time period. Moreover, the thickness of the film 8 is smaller than that assembled by the prior way.

Moreover, a center of the round disk 7 has an opening 71. A top of the opening 71 is flat. An inner wall 71b of the opening 71 is straight. When the shaft 61 at a lower end of the receiver 6 inserts into the opening 71, an axial surface of the shaft 61 is in surface-contact with the inner wall 71b and a bottom 68 of the receiver 6 is also in surface-contact with a top surface 71a of the opening 71. At this time, the elastic tightening ring 73 is compressed by an inner wall 71b of the opening 71 so as to induce a friction resisting force. By the elastic expanding force of the tightening ring 73, the round disk 7 is tightly engaged to the shaft 61 so that the round disk 7 can not drop out.

Besides, the upper cover 63 of the receiver 6 is integrally formed with the receiver 6. An outer diameter of the upper cover 63 is larger than that of the receiver 6. Thereby, the user can hold it conveniently. Moreover, a top surface of the upper cover 63 is formed with a groove 69. A bottom of the groove 69 is flatly placed with a name card 20 which is signed or having a number thereon. A transparent film 21 presses on the name card 20. The user can see the name or number on the name card through the transparent film 21. A diameter of the film 21 is equal to that the groove 69 so as not to drop out from the groove 69. Thereby, the film 21 has an effect of protecting the name card. The film 21 can be removed by fingers or other tools for updating the name card.

In above description, the receiver 6 and round disk 7 are made of metal, preferably, aluminum or aluminum alloy, or plastics by molding. Aluminum is light and thus is beneficial in molding. Moreover, when the round disk 7 has the same material as the film 8, the receiver 6 is disposable and reusable.

Figure 6:
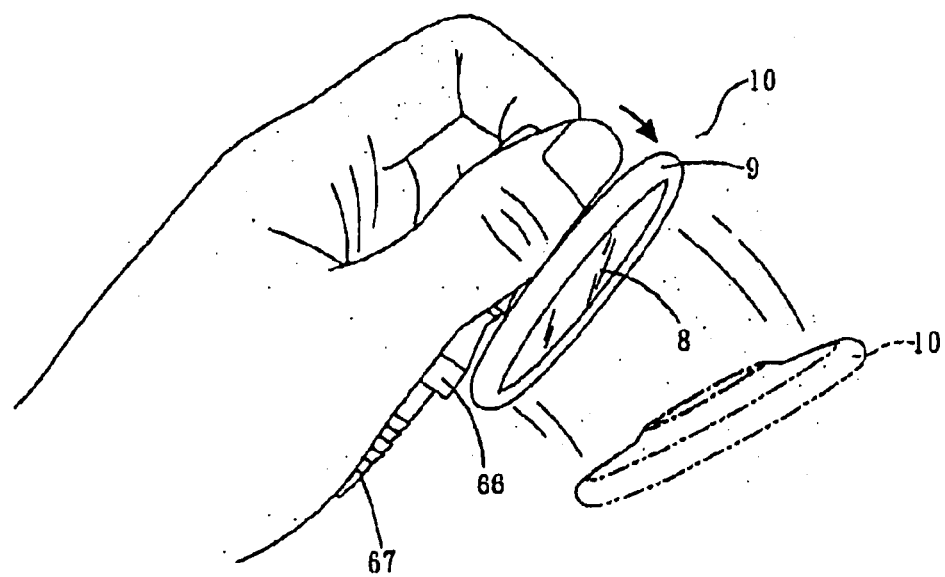
FIG. 6 is a schematic view showing that the receiver of the present invention can be updated rapidly.
Figure 7:
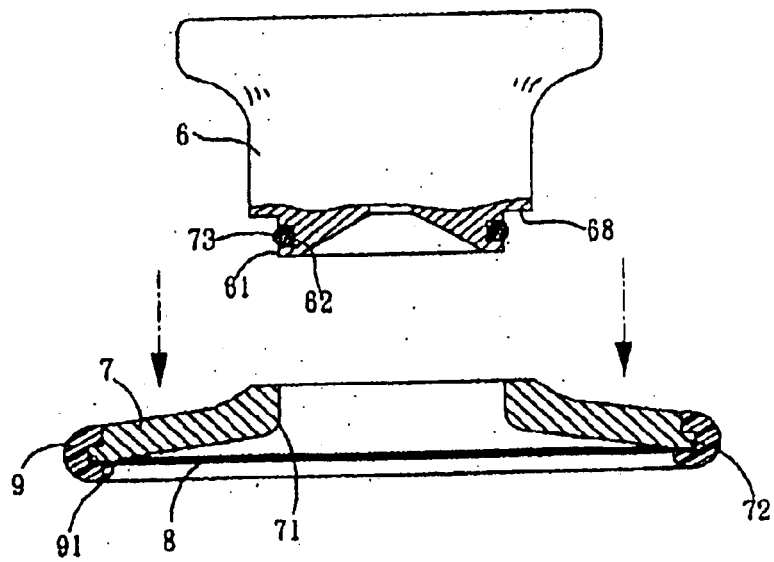
FIG. 7 is a schematic view showing the receiver of the present invention.

FIG. 6 is a schematic view showing the receiver 6 of the stethoscope receiver is separated from the main structure. It is illustrated that the listening disk 10 is fixed below the shaft 61 of the receiver 6. The user can hole the upper cover 63 of the receiver 6 by three fingers. When the fingers applies an downward force to the receiver 6, the listening disk 10 will separate from the shaft 61 gradually, as shown in FIG. 7. Namely, the apply force of the fingers is larger than the resisting force of the tightening ring 73, the round disk 7 will slide downwards. Once the tightening ring 73 is released, the listening disk 10 will separate from the shaft 61 rapidly. Otherwise, if the listening disk 10 is reassembled to be below the receiver 6, it is only necessary to flatly place the listening disk 10. Then, the shaft 61 is enforced into the opening 71 so as to complete the assembly work rapidly. Thereby, the assembling and detaching works of the listening disk 10 of the present invention is easy and rapid. Especially, even the listening disk 10 is not completely placed, and or the shaft 61 is shifted asides slightly. The shaft 61 can be enforced into the opening 71 for fixing. No prior art screw hole in the listening disk and no prior art stud at a lower end of the receiver are used for screwing. Thereby, the detaching and updating of the receiver 6 and listening disk 10 of the present invention are greatly improved.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A quick-updating stethoscope receiver comprising:

a receiver;

a listening disk at a lower end of the receiver; wherein the listening disk can be embedded into a lower end of the receiver;

an upper cover at a top end of the receiver; and a transducer combining at a lateral wall of the receiver and a connector at a rear end of the transducer; characterized in that:

a lower end of the receiver has an axial extended shaft; the shaft is formed with an annular trench; an elastic tightening ring is embedded into the trench; the tightening ring is made of rubber material and a diameter of a cross section of the tightening ring is larger than a depth at the trench so that part of the tightening ring protrudes out of the trench; the listening disk includes a staged round disk and a plastic film at a bottom of the round disk; a center of the round disk has an opening; when the shaft at a lower end of the receiver inserts into the opening, an axial surface of the shaft is in surface-contact with the inner wall and the elastic tightening ring is compressed by an inner wall of the opening so as to induce a friction resisting force; by the elastic expanding force of the tightening ring, the round disk is tightly engaged to the shaft so that the round disk can not drop out.

2. The quick-updating stethoscope receiver as claimed in claim 1, wherein the film is arranged at a bottom of the round disk and an elastic rubber ring encloses a periphery of the round disk for fixing the film.

3. The quick-updating stethoscope receiver as claimed in claim 2, wherein a periphery of the round disk is installed with annular flange and an inner edge of the elastic rubber ring is formed with an annular groove.

4. The quick-updating stethoscope receiver as claimed in claim 1, wherein the round disk is made with materials identical to those for manufacturing the film.

* * * * *